US00PP17174P2

(12) United States Plant Patent
Korlipara

(10) Patent No.: US PP17,174 P2
(45) Date of Patent: Oct. 24, 2006

(54) ***CAMPANULA* PLANT NAMED 'POWDER PUFF'**

(50) Latin Name: *Campanula persicifolia*
Varietal Denomination: Powder Puff

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/155,216

(22) Filed: Jun. 15, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct cultivar of *Campanula persicifolia* plant characterized by large, very double, white flowers and strong, thick stems.

1 Drawing Sheet

Botanical denomination: *Campanula persicifolia.*
Variety designation: 'Powder Puff'.

The present invention relates to a new and distinct cultivar of *Campanula persicifolia* plant and given the cultivar name of 'Powder Puff'. *Campanula* is in the family Campanulaceae. *Campanula persicifolia* 'Powder Puff' is a mutation of *Campanula persicifolia* 'Moorheimii', a commercial, unpatented plant. The naturally occurring branch mutation was found in the trial fields in Canby, Oreg.

This new and unique *Campanula persicifolia* is distinguished by:

1. Large, very double flowers
2. Strong thick stems
3. Pollen and seed sterility resulting in longer bloom time.

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Campanula persicifolia* 'Powder Puff' growing in the ground in the field in July in Canby, Oreg.

DETAILED PLANT DESCRIPTION

The following is a detailed description of the new *Campanula persicifolia* based on observations of one and a half year old specimen grown in a one gallon container in an open air shade house with 50% shade cover and added irrigation in the summer months in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Campanula persicifolia.*
Variety denomination: 'Powder Puff'.

Plant:
- *Form.*—Rosette-forming herbaceous perennial.
- *Hardiness.*—USDA Zone 4–8.
- *Size.*—54 cm tall and 27 cm wide to top of flowers.
- *Habit.*—Upright.
- *Vigor.*—Good.
- *Roots.*—Thick, fibrous, White 155A.

Stem:
- *Number.*—4–5, branching at each node.
- *Size.*—54 cm long to top of flowers and up to 10 mm wide at the base. Leafy only at the bottom 5 cm.
- *Color.*—Yellow Green 147B with lenticels in stem Grey Brown 199B.
- *Surface texture.*—Glabrous.

Leaf:
- *Type.*—Simple.
- *Arrangement.*—Alternate.
- *Shape.*—Variable. Lower leaves on bottom 5 cm of stem are oblanceolate to spatulate and have petioles. Stem leaves are lanceolate and sessile.
- *Venation.*—Pinnate.
- *Margins.*—Revolute, serrate.
- *Apex.*—Acuminate.
- *Base.*—Basal leaves are attenuate, stem leaves are auriculate.
- *Blade size.*—Variable, basal leaves are 4 to 9.5 cm long. Stem leaves are 3 to 10.5 cm long, decreasing in size going up the stem.
- *Surface texture.*—Glabrous, glossy, thick and leathery to the touch.
- *Petiole.*—0 to 6 cm long and 0 to 2 mm wide, glabrous, Yellow Green 147D.
- *Leaf color.*—Topside — Green 137A. Bottom side — Yellow Green 147B.

Inflorescence:
- *Type.*—Terminal raceme.
- *Number of racemes in first spring flush.*—8 to 10.

*Number of flowers per raceme.*—20.

*Pedicel.*—2 to 9 cm long and 2 mm wide, glabrous, Yellow Green 146B.

*Bloom period.*—June through August in Canby, Oreg.

Flower bud:

*Size.*—2.5 cm wide and 1.5 cm deep.

*Shape.*—Campanulate.

*Color.*—White 155A with Yellow Green 144C inner petals.

Flower:

*Type.*—Actinomorphic.

*Shape.*—Campanulate.

*Size.*—2.5 cm deep and 5.5 cm wide.

*Number of corolla layers.*—5 main with 5 to 7 lobes per layer, center of the flower has many more layers of petaloid segments.

*Petals.*—Broadly ovate, entire, tip mucronulate.

*Color.*—White 155D with green center, Yellow Green 144A, on both surfaces. Center petals have yellow green bases, Yellow Green 144C.

*Calyx.*—Rotate in shape, 5 to 7 lobes in 1 to a partial layer.

*Calyx size.*—3.5 cm wide and 5 mm deep.

*Calyx lobes.*—18 mm long, ovate, cupped, tips acuminate.

*Calyx color.*—Green 137B on both surfaces.

*Stamen number.*—0.

*Pistil color.*—No pistil, female sterile.

*Pollen color.*—No pollen, male sterile.

*Fragrance.*—Fresh.

*Lastingness.*—Each flower lasts for about 7 days on the plant.

Fruit and seed: None produced; plant is male and female sterile.

Diseases and pests: No diseases found of this new variety or on its parent plant. All *Campanula persicifolia* are susceptible to snails and slugs and aphids.

COMPARISON TO SIMILAR *CAMPANULA PERSICIFOLIA*

Compared to *Campanula persicifolia* 'Moorheimii' (an unpatented plant), *Campanula persicifolia* 'Powder Puff' is more double with green, petal-like segments instead of a pistil in the flower center and thicker broader leaves. The habit is the same but the stems are thicker, stronger, and somewhat shorter.

I claim:

1. A new and distinct *Campanula persicifolia* plant substantially as herein illustrated and described.

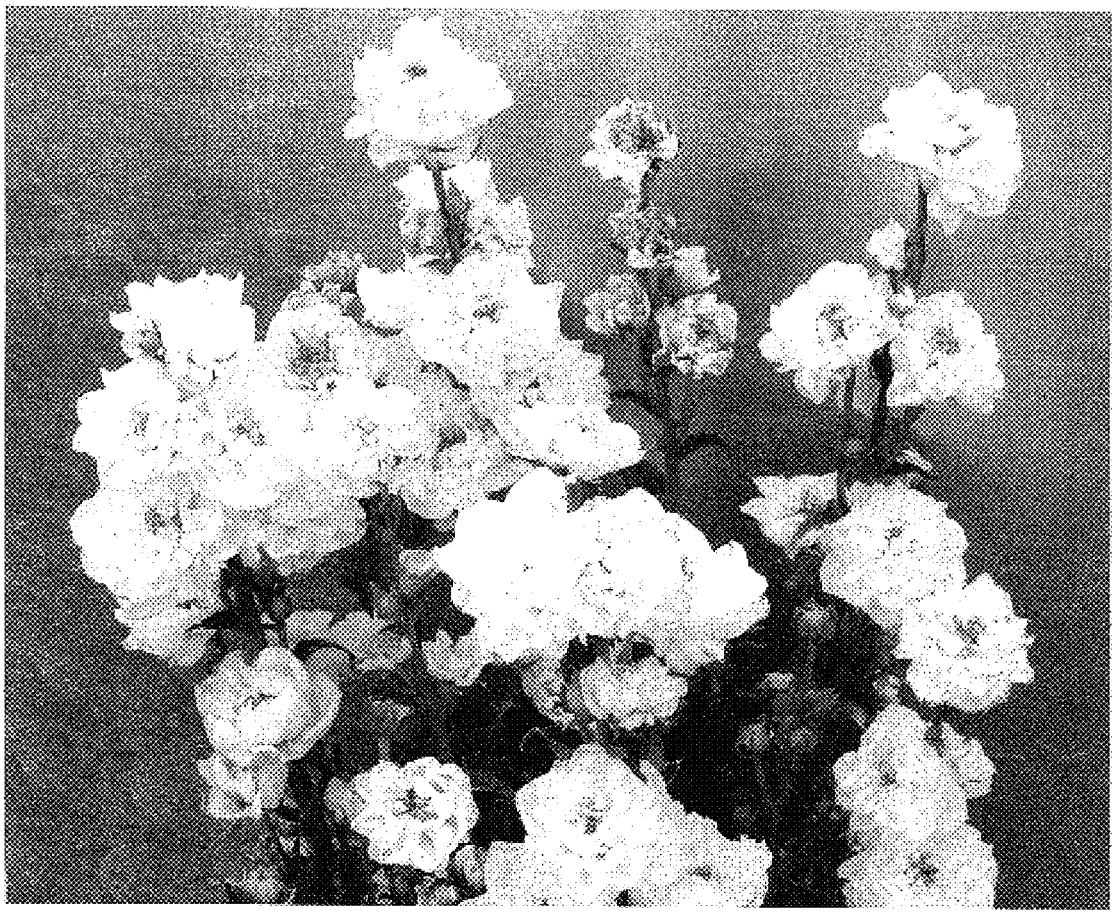

* * * * *